United States Patent
Kuwahata (10) Patent No.: US 11,957,902 B2
(45) Date of Patent: Apr. 16, 2024

(54) LIVING BODY STIMULATOR

(71) Applicant: Ryoji Kuwahata, Kanagawa (JP)

(72) Inventor: Ryoji Kuwahata, Kanagawa (JP)

( * ) Notice: Subject to any disclaimer, the term of this patent is extended or adjusted under 35 U.S.C. 154(b) by 74 days.

(21) Appl. No.: 17/213,915

(22) Filed: Mar. 26, 2021

(65) Prior Publication Data

US 2021/0213280 A1 Jul. 15, 2021

Related U.S. Application Data

(63) Continuation of application No. PCT/JP2019/015826, filed on Apr. 11, 2019.

(30) Foreign Application Priority Data

Oct. 1, 2018 (JP) .................. 2018-186750

(51) Int. Cl.
*A61N 1/06* (2006.01)
*A61N 1/04* (2006.01)
*A61N 1/36* (2006.01)

(52) U.S. Cl.
CPC .............. *A61N 1/06* (2013.01); *A61N 1/0452* (2013.01); *A61N 1/36003* (2013.01); *A61N 1/36034* (2017.08)

(58) Field of Classification Search
CPC ...... A61N 1/0452; A61N 1/0456; A61N 1/06; A61N 1/36003; A61N 1/3603;
(Continued)

(56) References Cited

U.S. PATENT DOCUMENTS

2004/0236391 A1 11/2004 Kobayashi et al.
2005/0277997 A1 12/2005 Ohta et al.
(Continued)

FOREIGN PATENT DOCUMENTS

JP H09-182805 7/1997
JP 2003-135607 5/2003
(Continued)

OTHER PUBLICATIONS

International Search Report and Written Opinion of PCT/JP2019/015826, dated Jul. 9, 2019, 10 pages including English translation of the International Search Report.

*Primary Examiner* — Carl H Layno
*Assistant Examiner* — Jane C Kalinock
(74) *Attorney, Agent, or Firm* — Hamre, Schumann, Mueller & Larson, P.C.

(57) ABSTRACT

A living body stimulator includes a low-frequency pulse generator, a high-frequency signal generator, a synthesizer for forming a synthesized waveform where a high-frequency signal of the high-frequency signal generator is superimposed on a low-frequency pulse signal of the low-frequency pulse generator, a waveform control signal circuit for controlling the synthesizer so that one cycle includes an ON period of the synthesized waveform where the high-frequency signal is superimposed on the low-frequency pulse signal and an OFF period where the high-frequency signal is not superimposed on the low-frequency pulse signal, and an output transformer for receiving the synthesized waveform. An impedance on an output side of the output transformer is set such that a voltage of the synthesized waveform gradually increases and decreases during the ON period on the output of the output transformer when pads connected to the output of the output transformer are attached to the living body.

2 Claims, 8 Drawing Sheets

(58) Field of Classification Search
CPC ............ A61N 1/36034; A61N 1/36175; A61N 1/36178; A61N 1/36189; A61N 1/36192; A61N 1/36196
USPC .......................................................... 607/48
See application file for complete search history.

(56) References Cited

U.S. PATENT DOCUMENTS

| | | | | |
|---|---|---|---|---|
| 2014/0067009 | A1* | 3/2014 | Turumaki | A61N 1/36071 607/48 |
| 2016/0184589 | A1* | 6/2016 | Li | A61N 1/36189 607/45 |
| 2016/0206877 | A1* | 7/2016 | Hargrove | A61B 5/4058 |

FOREIGN PATENT DOCUMENTS

| | | |
|---|---|---|
| JP | 2004-344444 | 12/2004 |
| JP | 2005-348859 | 12/2005 |
| JP | 2006-175166 | 7/2006 |
| JP | 2010-057805 | 3/2010 |
| JP | 2012-130502 | 7/2012 |
| JP | 5535405 B2 | 7/2014 |
| JP | 2016-202690 | 12/2016 |
| JP | 2017-086261 | 5/2017 |
| WO | 2013/008541 | 1/2013 |

* cited by examiner

LIVING BODY STIMULATOR

CROSS-REFERENCE TO RELATED APPLICATIONS

The present application is a continuation of International Application No. PCT/JP2019/015826, filed on Apr. 11, 2019, and based upon and claims the benefit of priority from Japanese Patent Application No. 2018-186750, filed on Oct. 1, 2018, the entire contents of which are incorporated herein by reference.

TECHNICAL FIELD

The present application relates to a living body stimulator that applies an electrical stimulation to a living body for effectively performing mainly a muscle training, muscle strengthening, muscle rehabilitation/treatment, fatigue recovery treatment, and the like.

BACKGROUND ART

It is widely known that, by bringing electrodes (pads) into contact with a surface of a living body and by applying such as electrical pulse waves or sine waves to the surface of the living body, an electrical stimulation is applied to muscles to obtain muscle activation and relaxation effects. The living body stimulator is used practically as electric treatment devices and health appliances. Such devices and appliances are used for various purposes such as the muscle stimulation, muscle rehabilitation, muscle training, body shape-up, relaxation, and treatments of the muscle pain, stiffness, numbness, low back pain, and fatigue recovery.

Many of the living body stimulators using the electrical stimulation adopt low-frequency pulses. The living body stimulator causes a low-frequency pulse current to be flowed between two or more electrodes arranged on the living body to stimulate the muscle between the electrodes, and facilitates a blood flow of the muscle by repeating the contraction and relaxation of the muscle. This enables the acquisition of exercise effects such as the physical shoulder tapping, massage, and muscle training.

A pulse wave of several Hz to several tens of Hz is used as a low-frequency pulse of an electric treatment device or the like. By changing the voltage intensity and the pulse width of the pulse, an on/off interval of the generated pulse, and the like for combination, a pulse waveform suitable for various use purposes such as modes of the shoulder tapping, muscle strengthening, and relaxation is formed. For example, a currently commercially available low-frequency treatment device or the like generates a reference pulse with a pulse width of 0.2 msec to several msec and a pulse voltage of 10 to 20 V. In the shoulder tapping mode, the device causes a generation interval of the reference pulse to be at intervals of several msec to several seconds to generate the reference pulse depending on the preference of a user, and accordingly, a desired shoulder tapping effect is obtained. Further, in modes of massage effects and relaxation effects, the above described ten to several tens of reference pulse groups are generated continuously for 1 second to several seconds or are stopped in an alternative manner to obtain a hand massage effect.

Although the definitions of the low frequency and the high frequency are not clear, in this industry (in a field of electric treatment), a frequency of several Hz to several hundreds of Hz is often used as the low frequency, and a frequency of several hundreds of Hz or above is called a high frequency (including a band frequency called a medium frequency). In the present application, descriptions are given based on these frequency ranges. When the above described low-frequency pulse is applied to the muscle, the muscle is stimulated and is contracted. Thereafter, when the pulse wave is stopped, the muscle starts relaxing. In the shoulder tapping mode and the like, the low-frequency pulse of several Hz to several tens of Hz is used. Each time the low-frequency pulse is applied to the muscle, the muscle is relaxed, and a user can obtain shoulder tapping effects with a feel of "turn, turn, . . . ". The frequency of the low-frequency pulse is increased so that a next pulse is continuously applied to the muscle before the relaxation of the muscle. This keeps the contraction state of the muscle, and by setting an interval state in which the pulse is stopped, the muscle becomes relaxed, and the effect of the slow massage is produced.

It is considered that the muscle of the living body contracts and relaxes by a nerve impulse, and the energy source of the muscle contraction increases by performing the muscle training. In other words, muscle fibers become thick and blood vessels develop also by performing the training. When each muscle fiber becomes thick, the muscle protein which is the composition of the muscle and a substance which is an energy source of the muscle contraction such as glycogen increases. The muscle is repeatedly contracted and relaxed by intermittently applying the electrical stimulation to the muscles, and thus, various types of living body stimulators for performing the muscle training and muscle strengthening by using the effect are proposed.

For this kind of living body stimulator, a method for performing the muscle training and muscle strengthening by using a rectangular wave pulse by the low frequency is generally proposed. Patent Document 1 (JP 2016-202690 A) discloses a method for a living body stimulator to apply the electrical stimulation to the muscle to combine some (2 Hz, 4 Hz, 8 Hz, 16 Hz, 20 Hz and the like) of burst waveforms of 20 Hz or less and to cause the muscle to be contracted alternately and repeatedly for a fixed period of time.

The muscle training device using the low frequency as described above has an effect on the muscle, but the stimulation from the device is diffused on a skin surface layer, and thus, the device is mainly used for an outer muscle (or also is referred to as a superficial muscle). Therefore, as a method for stimulating a more inner muscles, Patent Document 2 (JP 2006-175166 A) discloses a method of using a frequency of 1 kHz to 20 kHz (in Patent Document 2, such frequency range is referred to as a medium frequency) which is higher than the low frequency described above. For example, disclosed is a muscle training device using the electrical stimulation, which includes at least two pairs of electrodes that output a sine wave signal of a medium frequency to a body, and has portion modes having a first mode for use in such a state that electrical signals from the pairs of electrodes intersect at a predetermined portion of the body, and a second mode for use in such a state that electrical signals from one or both of the pairs of electrodes do not intersect at the predetermined portion of the body.

Further, as an improved version of the muscle training device using a frequency higher than the low frequency, a muscle stimulator using an interference wave is also proposed. For example, Patent Document 3 (JP 2005-348859 A) discloses a muscle training device that includes an electrical stimulation output unit that designates and inputs the magnitude and a frequency of an electrical stimulation signal, generates the electrical stimulation signal based on the designation, and conveys the electrical stimulation signal to the body of the user via a plurality of electrodes to cause the interference wave to be generated, a storage unit which stores current frequency correlation data representing the relationship between the magnitude and the frequency of the electrical stimulation signal, an operation unit which receives an instruction from the user, and control means which determines the frequency based on the current frequency correlation data and outputs the magnitude and the frequency of the electrical stimulation signal to the electrical stimulation output unit based on the magnitude of the electrical stimulation signal of the user instruction received through the operation unit.

It is recognized that, while the living body stimulator using the low frequency stimulates about several millimeters of a superficial layer portion of the living body, the living body stimulator using the higher frequency, the medium frequency, or the interference wave can stimulate a deeper layer portion. It is needless to say that a method of stimulating the inside of the living body by increasing the applied voltage is possible, but if such the method is adopted, feelings of pain and tingle are caused as a feeling of use, and thus, the living body stimulator using the low frequency and medium frequency described above is mainly used for the muscle training of the superficial layer portion of the living body that is called the outer muscle, and is not used for the muscle activation of the inner muscle (also referred to as deep muscle).

A structure of the living body (a human body or an animal) is electrically composed of a capacitor (capacitance) component and an impedance (resistance) component, and thus, it is considered that, as the frequency becomes high, the electrical signal more easily passes through the inside of the living body. If only the high frequencies is adopted, the user may not feel the stimulation enough for contracting the muscle, and thus, the high frequency alone is not practically used in the muscle training. However, a method is proposed in which the stimulation is applied to a deeper layer by using a synthesized waveform in which a high frequency is superimposed on a low-frequency pulse. Patent Document 4 (JP 2010-057805 A) discloses a living body stimulator in which electrodes are brought into contact with the living body to flow a current from the electrodes to the living body and stimulate the living body, and the high-frequency pulse is superimposed on the low-frequency pulse to stimulate the living body. It is known that a living body stimulator using such synthesized waveform can stimulate a further deeper layer than the living body stimulator using the low frequency.

Although the method using the synthesized waveform has an effect of reaching the deep muscle by the high-frequency component, the stimulation on the living body is too strong and the user feels a sense of discomfort during use, and thus, to reduce such the sense of discomfort, Patent Document 5 (JP 5535405 B2) discloses a method of applying a soft stimulation to the muscle by using a waveform in which a rectangular wave and a triangular wave are superimposed on the low-frequency pulse for the synthesis and the level of the high frequency is gradually increased or decreased.

However, in the method, the rectangular wave and the triangular wave are superimposed on the low-frequency pulse, and the low-frequency pulse is synthesized with the high-frequency signal, and thus, not only a circuit becomes complicated, but also noise (particularly, noise components by overshoot and undershoot) occurs when the superimposed low-frequency pulse and the high-frequency signal are synthesized. Therefore, if the method is applied to the muscle training of the deeper layer portion, the user feels pain or a sense of discomfort due to the noise. In addition, it is unclear how an efficient and effective muscle training result can be obtained when such the living body stimulator is applied to muscle training. Therefore, there is a demand for a living body stimulator using the synthesized waveform that can be continuously used for the muscle training of the deeper layer portion called an inner muscle to obtain positive results without causing the sense of discomfort or stimulation to the user.

SUMMARY

A main object of the present application is to provide a living body stimulator which applies an electrical stimulation to an inner muscle (a deep muscle) of a living body to apply the electrical stimulation not only to a superficial muscle but also to both of the deep muscle called a trunk muscle and the superficial muscle, and performs the muscle tightening, increasing of the muscle strength, and the muscle strengthening without causing the pain or a sense of discomfort to the user due to noise.

Further, an object of the present application is to provide a living body stimulator which is applied to a trunk muscle to strengthen the trunk muscle so that a muscle exercise capacity is improved and the muscle strength is increased.

Further, an object of the present application is to provide a therapeutic rehabilitation device used for the improvement/rehabilitation of the weakened muscle force by applying the living body stimulator to various inner muscles of the living body.

Also, an object of the present application is to provide a device for generating a living body stimulation signal waveform and a living body stimulator, which enable the acquisition of a stimulation effect on the inner muscle (the deep muscle) at a further deeper layer while providing a soft sensory stimulation.

Still further, an object of the present application is to provide a living body stimulator which can generate a living body stimulation complex signal waveform for stimulating the inner muscle with a soft feeling of stimulation by the combination and deformation of the variable synthesized waveform group and the fixed synthesized waveform group so that various waveforms depending on a wide range of use purposes such as the muscle training and relaxation of the deep muscle and the superficial muscle can be formed with a simple circuit configuration, and accordingly, the living body stimulator has an excellent shape-up (reduction in the waist circumference, slimming) effect by the muscle tightening.

To solve the above described problem, a living body stimulator according to an embodiment includes a low-frequency pulse generator configured to generate a low-frequency pulse signal wave, a high-frequency signal generator configured to generate a high-frequency signal wave, a synthesizer configured to form a synthesized waveform in which the high-frequency signal wave generated by the high-frequency signal generator is superimposed on the low-frequency pulse signal wave generated by the low-frequency pulse generator, and apply an electrical stimulation by the synthesized waveform to a living body, a controller configured to control the synthesizer so that one cycle is configured from an ON period of the synthesized waveform in which the high-frequency signal wave is superimposed on the low-frequency pulse signal wave and an OFF period in which the high-frequency signal wave is not superimposed on the low-frequency pulse signal wave, and an output transformer configured to receive the synthesized waveform. An impedance on an output side of the output transformer is set such that a voltage of the synthesized waveform gradually increases and decreases during the ON period of the synthesized waveform on the output side of the output transformer when one or more pairs of pads connected to the output side of the output transformer are attached to the living body. The controller is configured to control the synthesizer such that at least a part of the synthesized waveform is configured from a variable synthesized waveform group in which at least one of the ON period and the OFF period is varied at a low-frequency cycle.

By using the synthesized waveform in which the low-frequency pulse signal wave and the high-frequency signal wave are superimposed, an effect of the stimulation reaching the inner muscle (the deep muscle) can be obtained and also an effect of the stimulation on the outer muscle (the superficial muscle) is generated, and accordingly it is possible to efficiently obtain a muscle strengthening effect by training the trunk muscle. Further, the synthesized waveform is not a waveform formed by synthesis with a rectangular wave, a triangular wave and the like in which the high-frequency signal is superimposed, but a waveform in which the synthesized waveform is gradually increased or decreased is formed by setting the impedance on the output side of the output transformer, and therefore, the living body stimulator can be constituted with a simple circuit and without the overshoot and a downshoot, a waveform with a soft feeling and without a sense of discomfort can be obtained, and the living body stimulator which can bear the continuous use can be provided.

Furthermore, a state is formed in which the ON period and the OFF period of the synthesized waveform signal are varied at the low-frequency cycle, and by varying the variable synthesized waveform itself at the low-frequency cycle, the stimulation on the outer muscle is enhanced in addition to the stimulation on the inner muscle by the high-frequency signal wave.

A living body stimulation waveform for applying the synthesized waveform to the living body may be a repetitive waveform formed from a combination of the variable synthesized waveform group and a fixed synthesized waveform group in which the ON period and the OFF period are fixed.

In the living body stimulation waveform, the simultaneous stimulation on the inner muscle and the outer muscle by the variable synthesized waveform, and the stimulation mainly on the inner muscle by the fixed synthesized waveform are repeated so as to obtain a muscle exercise effect by tightening mainly the inner muscle and also the outer muscle, and obtain the comprehensive strengthening of the muscle force corresponding to the abdominal muscle exercise.

The controller may be configured to control the synthesizer such that at least a part of the synthesized waveform is configured from the variable synthesized waveform group in which a level of the ON period is varied at the low-frequency cycle.

A state is formed in which a level of the variable synthesized waveform is varied at the low-frequency cycle, and thus, it is possible to obtain an effect of the stimulation on the inner muscle and also a further stimulation effect on the outer muscle by tightening the outer muscle.

A period of the fixed synthesized waveform group may be set to be in a range from 40% to 100% of a period of the variable synthesized waveform group.

The period of the fixed synthesized waveform group is set to be in the range from 40% to 100% of the period of the variable synthesized waveform group, and thus, it is possible to obtain an effect of a muscle exercise of tightening mainly the inner muscle and also the outer muscle.

The living body stimulation waveform may be formed from a combination of the variable synthesized waveform group with an application time of 2 to 10 seconds and the fixed synthesized waveform group with an application time of 1 to 4 seconds.

An optimum muscle tightening effect can be obtained by setting the application time of the variable synthesized waveform and the application time of the fixed synthesized waveform to be a predetermined time.

A rest period may be provided between a period of the variable synthesized waveform group and a period of the fixed synthesized waveform group.

An optimum muscle tightening effect can be obtained by providing the rest period between the period of the variable synthesized waveform group and the period of the fixed synthesized waveform group.

The living body stimulator according to the embodiment is expected to be effective in preventing and rehabilitating the swallowing by applying to the throat muscles, is expected to be effective in rehabilitating the urinary incontinence by applying to the bladder detrusor muscles and the pelvic floor muscles, and can improve the balance function against the locomotive syndrome by applying to the iliopsoas muscles and the thigh muscles. The improvement and rehabilitation effects of various symptoms caused by the reduction in the muscle force of the inner muscle can be widely expected. Furthermore, these functions are used to effectively tighten the inner muscle and the outer muscles, and the living body stimulator is applied to the shape-up and the preventive medicine so that various effects such as body shape maintenance, cosmetic correction, and aging prevention can be expected.

Further, with the living body stimulator according to the embodiment, the synthesized waveform is attached to the living body, and a waveform as the living body stimulation does not have the overshoot in which the stimulation is gradually increased or the downshoot in which the stimulation is gradually decreased, and thus, it is possible to obtain different varieties of stimulation effects with the soft feeling and with little tingle compared to the stimulation feeling (feelings of the prick pain or tingle) by a conventional pulse. Therefore, the user feels a little sense of discomfort when using the device, and the device has an effect that the device can be used for a long hours or continuously as a muscle training device.

It should be noted that by applying the living body stimulator according to the embodiment to other treatments, rehabilitations, massages, and beauty treatments by any combination of the above components, the embodiment is effective as another embodiment within the scope of the present application.

DETAILED DESCRIPTION

For the training of muscle functions and the muscle strengthening performed in various sports and rehabilitations, if a load is applied to the muscle, the muscle fibers become thick, and when the muscle fibers become thick, the muscle protein which is the composition of the muscle and a substance which is an energy source of the muscle contraction such as glycogen increase. The maximum muscle force is proportional to the thickness of the muscle fiber, and as the muscle fiber becomes thick, the greater force can be generated. The muscle force is considered to be adjustable depending on the number of muscle fibers, and the maximum muscle force means that all muscle fibers are active. It is considered that the half of the muscle fibers are involved when the half of the muscle force is exerted and alternatively the other half of the muscle fibers are inactive. These muscle fibers are associated with nerves, and the nerves work to activate or deactivate the muscle fibers.

In the muscle strengthening, muscle tightening, and muscle rehabilitation, the muscle fibers are thickened by applying a physical load to the muscles, but for example, in a case of a sick person or an elderly person who has no physical strength to bear the training or rehabilitation, or a person who has no time for performing the training or rehabilitation, or a person who wants to obtain a result effectively in a short period of time, it is known that if the contraction and relaxation of the muscle are repeated by applying an electrical stimulation to the muscle by using a living body stimulator, the same effect as application of the physical load can be obtained.

In general, the muscle strengthening and the muscle tightening require three conditions that are condition of (1) an exercise intensity, (2) a duration, and (3) a repetitive exercise. The exercise intensity is the amount of exercise loads to be applied to the muscle, and is set based on the maximum muscle force. The duration is the number of seconds during which the training is continued relative to the training intensity. Also, the repetitive exercise is at how many hours (days) intervals, the repetition of the muscle training is performed. The present application is based on the verification results obtained by realizing these training conditions with the living body stimulator.

With respect to the condition of the exercise intensity, as for how the exercise load is applied to the muscle in the muscle training, the maximum muscle force (RM=Repetition Maximum) is calculated, and the amount of the exercise load to be applied to the muscle during the training is programmed based on the maximum muscle force. The maximal muscle force is a limit value of the muscle force that can be exerted at one time, and how many times a user can continuously lift a weight (such as a bench press) of a certain weight is measured. For example, if a user lifts a maximum of 100 kg of the weight at one time, the maximum muscle force (1 RM or 100% RM) of the user is 100 kg, and based on the maximum muscle force, how many % of the exercise intensity is used for performing the training is set. Training programs vary depending on the muscle force of each user and purposes, but in the most commonly used programs, 1 to 4 RM (100% RM to 90% RM) is used for the muscle strengthening, 5 to 14 RM (90% RM to 70% RM) is used for the muscle hypertrophy, and 15 to 25 RM (70% RM to 60% RM) is used for the endurance. In other words, it is effective to perform the continuous repetitions 4 times or less with 90% or more of the maximum muscle force for the muscle training, perform the continuous repetitions from 5 to 14 times with 90 to 70% of the maximum muscle force for the muscle hypertrophy, and perform the continuous repetition exercise from 15 to 25 times with 70% to 60% of the maximum muscle force to increase the endurance.

There are many studies for the condition of the duration, but "Hettinger theory" is often used for the muscle training. The theory shows how much muscle contraction duration should be spent for the maximum muscle force to be effective. For the maximum muscle force (100% RM), about 2 to 4 seconds is enough, but the effect is considered to be weakened if the time is 2 seconds or less. Further, for 90% to 80% of the maximum muscle force, 4 to 6 seconds are required, for 70% to 60% of the maximum muscle force, 6 to 10 seconds are required, and for 50% to 40% of the maximum force, 15 to 20 seconds are required.

In addition, with respect to the condition of the repetitive exercise, as to how many hours (days) are set as the training interval, effects are considered to be accumulated by performing the next training while the previous training effect remains. In general, it is considered that the effect is slightly reduced if the next muscle training is performed one day after the previous training, but the effect is reduced by half if the next muscle training is performed one week after the previous training, and the effect is returned almost to the original state before performing the previous muscle training if the next muscle training is performed two weeks after the previous training.

In a living body stimulator, an electrical stimulation is applied to the muscle, and by intermittently turning on and off the electrical stimulation, the muscle is contracted and relaxed, and this is equivalent to the activation of the contraction and relaxation of the muscle by the nerve impulse in the case of the muscle. However, while the number of muscle fibers applied with the nerve impulse (momentum) by the actual muscle can be adjusted, it is not possible to stimulate each muscle fiber with the electrical stimulation, and effects similar to effects of applying the nerve impulses are generates for any of the muscles applied with the electrical stimulation.

Accordingly, in order to apply the condition of the exercise intensity to the electrical stimulator, a certain level of adjustment is possible by adjusting a signal level to be applied. The range is limited, and at a signal level equal to or above a level that the human body feels the signal, in the range applied with the signal of the electrical stimulation, a signal corresponding to the nerve impulse is basically provided to all of the muscle fibers, and the muscle force becomes at least close to the maximum muscle force (100% RM). It is assumed that the exercise intensity becomes the exercise intensity of at least 80% RM or above of the maximum muscle force.

In order to apply the condition of the duration to the muscle training or rehabilitation by using the electrical stimulator, the application time of the electrical stimulation is determined based on "Hettinger theory". In other words, if a pulse signal at or above a level that the human body feels the signal is applied, the muscle applied with the signal has a contraction action corresponding to or close to the maximum muscle force. For this reason, as described above, it is considered that the intensity of exercise holds at least 80% RM or more of the maximum muscular force when the signal intensity that the human body feels the signal is provided, and it is effective to set the continuous application time of the synthesized waveform as the duration to be about 2 seconds or above and 10 seconds or less, but no effect is observed at 2 seconds or less.

Furthermore, the condition of the repetitive exercise is at what intervals (days and hours), the electrical stimulator is used, and how the effect of the training continues is almost the same in the training using the electrical stimulation also, and effects are accumulated by continuously performing a next training before effects of the previous effect become zero.

Embodiment

Figure 1:
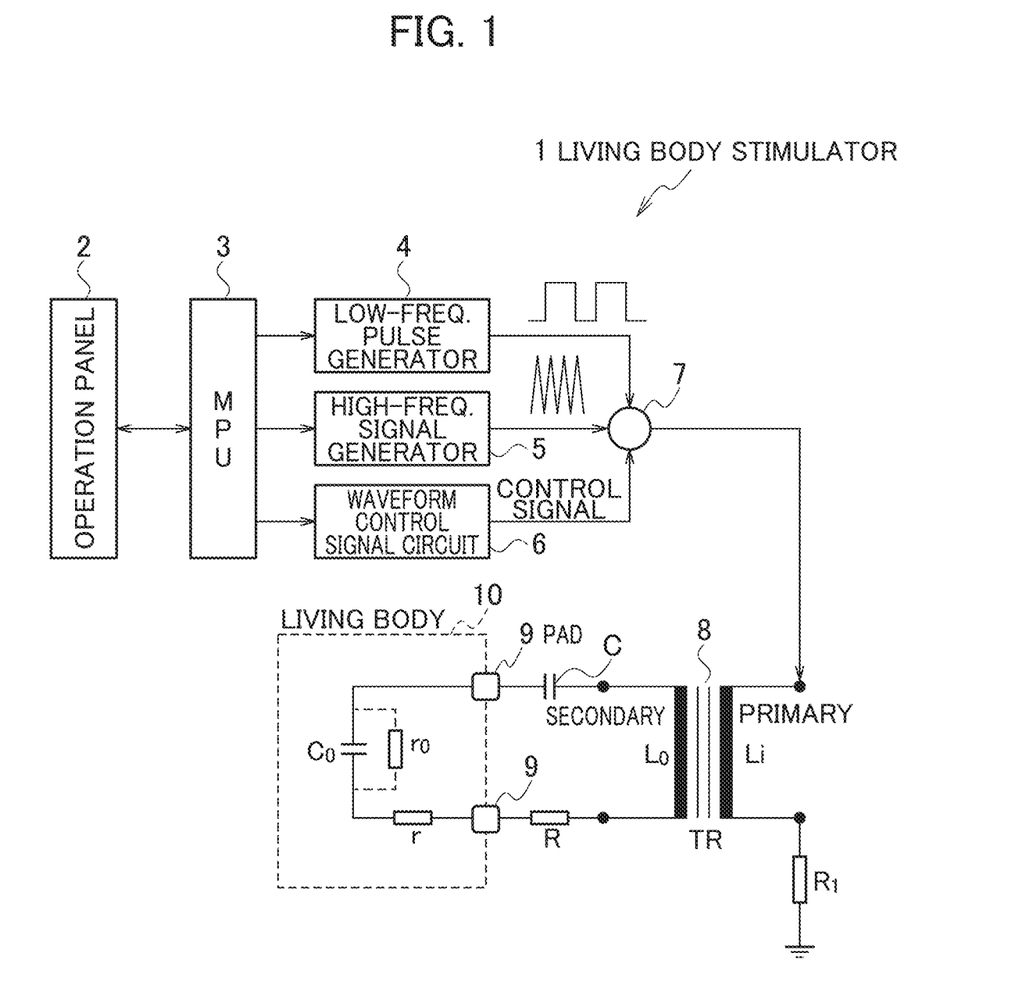
FIG. 1 is a circuit configuration diagram of a living body stimulator according to an embodiment.

By taking into consideration of the above described conditions and assumptions, an embodiment obtained by embodying a living body stimulator according to the present application that electrically stimulates a living body will be described with reference to the drawings. The drawings are schematically illustrated for the convenience of explanation. FIG. 1 is a circuit configuration diagram of a living body stimulator according to the embodiment. The embodiment according to the present application will be described by assuming that the use purpose of the device is mainly for the muscle training.

In FIG. 1, the living body stimulator 1 includes an operation panel 2, a microcomputer (CPU or MPU) 3, a low-frequency pulse generator 4, a high-frequency signal generator 5, a waveform control signal circuit 6, a synthesizer 7, and an output transformer (TR) 8. A user selects and inputs, through the operation panel 2, various modes such as modes of the muscle training, shape-up, and relaxation depending on the use purpose of the living body stimulator 1. Further, the user inputs, through the operation panel 2, an operation time (timer setting), intensity selection, and the like. The microcomputer (CPU or MPU) 3 controls the low-frequency pulse generator 4, the high-frequency signal generator 5, and the waveform control signal circuit 6 so that a living body stimulation waveform suitable for each use purpose is formed in response to an instruction signal input through the operation panel 2.

The microcomputer 3 is programmed so as to form the living body stimulation waveforms suitable for modes of various use purposes. The determination of each mode is made by a combination of parameter changes such as a high-frequency component to be synthesized, a low-frequency pulse component to be synthesized, an ON period in which the high-frequency component and the low-frequency component are synthesized and output, an OFF period in which the output of the synthesized waveform is stopped, the signal intensity, the number of repetitions, and control conditions for changing the synthesized waveform in which the high-frequency signal and the low-frequency pulse are synthesized at a low frequency.

After a desired mode, an operation time, intensity, and the like are selected through the operation panel 2, the microcomputer 3 instructs each of the low-frequency pulse generator 4, the high-frequency signal generator 5, and the waveform control signal circuit 6, that form the synthesized waveform, and controls the high-frequency component, the low-frequency pulse component, the ON period, the OFF period, and the like according to the selected mode.

As an example, the low-frequency pulse generator 4 generates a rectangular wave pulse signal (a low-frequency pulse signal wave) in a range from several Hz to several tens of Hz. It is enough if the frequency of the low-frequency pulse is in a range from about several Hz to several hundreds of Hz, and the frequency may be switched or varied depending on the use purpose. The high-frequency signal generator 5 generates a signal (a high-frequency signal wave) of 10 kHz or above. In the embodiment, an output signal of 500 kHz by a sinusoidal oscillator is used as an example. The synthesizer 7 superimposes the high-frequency signal wave generated by the high-frequency signal generator 5 on the low-frequency pulse signal wave generated by the low-frequency pulse generator 4 to form a synthesized waveform. The waveform control signal circuit 6 corresponds to the controller of the present application and controls the synthesizer 7 such that the ON period in which the high-frequency signal wave is superimposed on the low-frequency pulse signal wave and the OFF period in which the high-frequency signal wave is not superimposed on the low-frequency pulse signal wave of the synthesized waveform from one cycle, and at least a part of the synthesized waveform is formed of a variable synthesized waveform group obtained by varying at least one of the ON period and the OFF period at a low-frequency cycle in accordance with an instruction from the microcomputer 3. More specifically, the waveform control signal circuit 6 controls the unit so that the high-frequency signal wave is superimposed on the low-frequency pulse signal wave during the ON period of the low-frequency pulse signal wave, and alternatively the high-frequency signal wave is not superimposed on the low-frequency pulse signal wave during the OFF period of the low-frequency pulse signal wave, generates a waveform control signal for temporally varying or varying the synthesized waveform in terms of levels, or for varying the synthesized waveform both temporally and in terms of levels to form the variable synthesized waveform group, and controls the synthesizer 7 based on the waveform control signal.

Figure 2A:
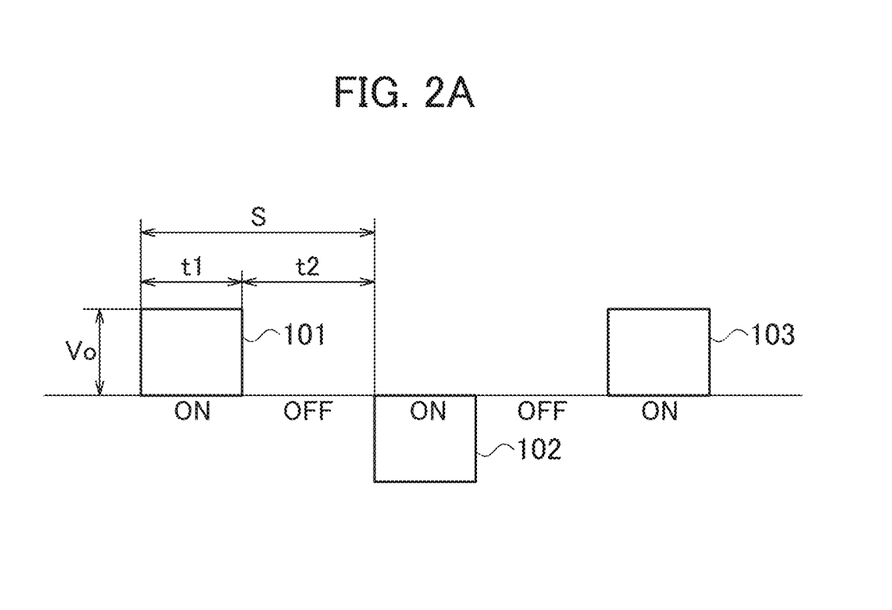
FIG. 2A is a waveform diagram of a low-frequency pulse signal wave of the living body stimulator according to the embodiment.

The microcomputer 3 sets an ON period t1, an OFF period t2, a level V0, and the like of the low-frequency pulse signal wave as illustrated in FIG. 2A based on the basic settings such as the use modes of the muscle training, shape-up, and relaxation, the intensity, and a timer instructed on the operation panel 2. The microcomputer 3 has well-known functions such as a crystal oscillator, a timer, a storage device, and an arithmetic processing unit, and achieves predetermined patterns of various modes programmed on the storage device by a control sequence. In each mode, the physical sensation applied to the living body is changed by changing the ON period (a synthesized waveform superposition period) t1, the OFF period (a synthesized waveform rest period) t2, and the output level V0 of the low-frequency pulse signal wave, and the repetition times of the cycle lengths. In the drawing, the cycle length of the low-frequency pulse signal wave is illustrated as an S period (one cycle) which is the sum of the ON period t1 and the OFF period t2.

The ON periods and the OFF periods of the low-frequency pulses 101, 102, 103, . . . are repeated for the cycle lengths S1, S2, S3, . . . respectively in FIG. 2A, and, in the ON state, sides and directions of pulse polarities are alternately changed between the upper side (the positive direction) and the lower side (the negative direction). Several change patterns are conceivable such as a case where, as illustrated in FIG. 2A, for individual cycle lengths, the directions of the pulse polarities are alternately changed between the positive direction and the negative direction, a case where all of the pulse polarities are in the same direction, or a case where the pulse polarities are in the positive direction for a certain period of time and are in the negative direction for a certain period of time. By randomly combining the polarities of the low-frequency pulses, the direction of the synthesized waveform in which the high frequency is superimposed on the low-frequency pulse signal wave during the ON period of the low-frequency pulses signal wave is changed, and accordingly, the physical sensation is changed.

As an output signal of the high-frequency signal generator 5, a sine wave signal of 500 kHz is used, but a waveform of the signal may be that of a high-frequency pulse signal or a high frequency rectangular wave signal. Further, as the frequency of the high-frequency signal becomes high, the deeper portion of the living body may be reached, and thus, an effect on an inner muscle can be adjusted by varying the frequency.

Figure 2B:
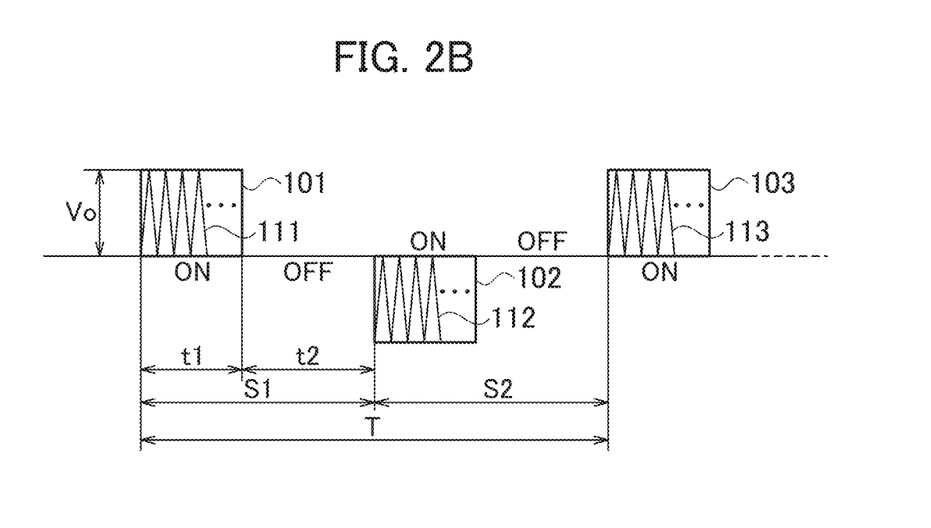
FIG. 2B is a waveform diagram of a synthesized waveform in which a high-frequency signal is synthesized with the low-frequency pulse signal wave of the living body stimulator according to the embodiment.

The waveform control signal of the waveform control signal circuit 6 is controlled such that the high-frequency signal is superimposed on the low-frequency pulse to form a synthesized waveform signal during the ON period of the low-frequency pulse signal wave and alternatively the formation of the synthesized waveform signal is stopped during the OFF period, and controlled the synthesized waveform on the upper side (in the positive direction) or on the lower side (in the negative direction). By this waveform control signal, the high-frequency signal is synthesized with the low-frequency pulse signal wave in the synthesizer 7 to output the synthesized waveform illustrated in FIG. 2B. The synthesized waveform illustrated in FIG. 2B has the ON period t1 in which the high-frequency signal wave 111, 112, 113, . . . is superimposed on the low-frequency pulse signal wave 101, 102, 103, . . . and the OFF period t2 in which the high-frequency signal wave 111, 112, 113, . . . is not superimposed on the low-frequency pulse signal wave 101, 102, 103, . . . , and the ON period t1 and the OFF period t2 form one cycle S1, S2, and so on.

Figure 4:
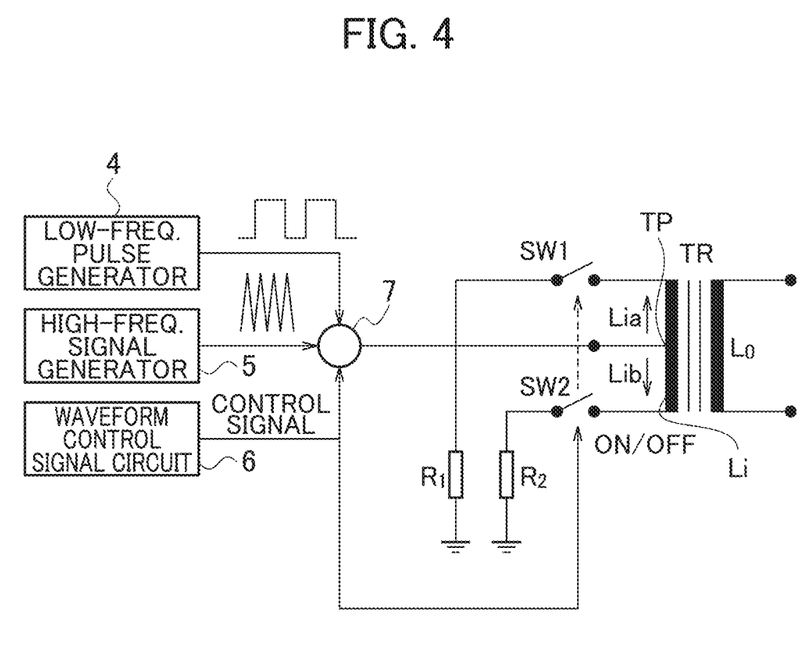
FIG. 4 is a specific circuit configuration diagram of the living body stimulator according to the embodiment.

The synthesizer 7 supplies the synthesized waveform to a primary coil Li of an output transformer 8. The output transformer 8 is insulated from a secondary coil Lo, and noise pulses, shock waves and the like caused on the primary side are alleviated. As illustrated in FIG. 4, it may be configured such that an intermediate tap TP is provided to the primary coil Li and by performing the alternative switching between a switch SW1 and a switch SW2, the upper side (the positive direction) and the lower side (the negative direction) of the synthesized waveform signal are switched.

The output of the secondary coil Lo of the output transformer 8 is connected to a pair of pads (or electrodes) 9 via a DC cut-off capacitor C and a line resistance R. The pair of pads 9 are used by contacting on a skin surface of a target muscle such as a muscle to be strengthened. The pads 9 are made from an electrically conductive material and is used in a manner that the pads are absorbed on the skin surface, but a gel or the like may be used to ensure the conductivity. Further, although the number of pads 9 may be two by adopting a pair of pads, by providing a plurality of pads that is one or more pairs of pads, a plurality of portions may be stimulated or the stimulated portions may be specified.

The living body 10 has a capacitive reactance, and an equivalent circuit, as illustrated in the living body 10, includes a capacitance Co, a slight or negligible level of resistance component ro parallel with the capacitance Co, and a resistance component r of the living body. If the pads 9 are attached on the skin surface of the living body 10, the capacitive reactance between the pair of pads varies depending on the distance between the pads, a dielectric constant of the living body 10, and the like. The capacitive reactance also largely varies depending on a contact state between the pads 9 and the living body. For the above reason, although an accurate grasping is difficult, in a human body model of ESD (Electro Static Discharge) standard, 670 pF is set as a standard.

Figure 5A:
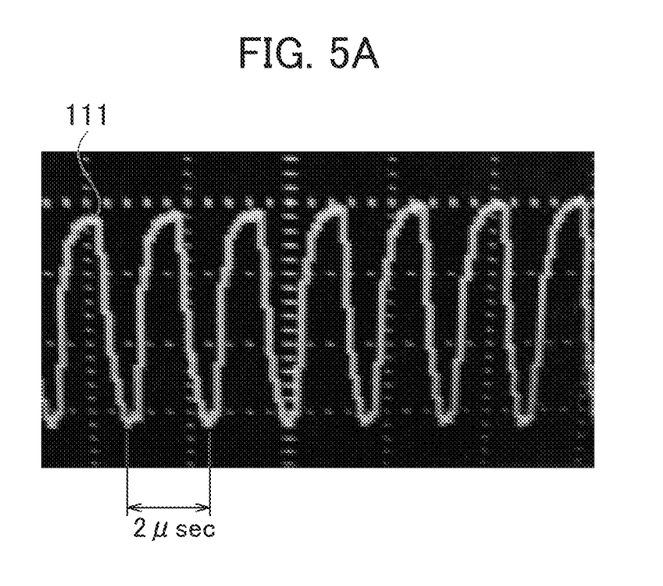
FIG. 5A is a diagram illustrating an example of an output signal of a high-frequency signal generator of the living body stimulator.
Figure 5B:
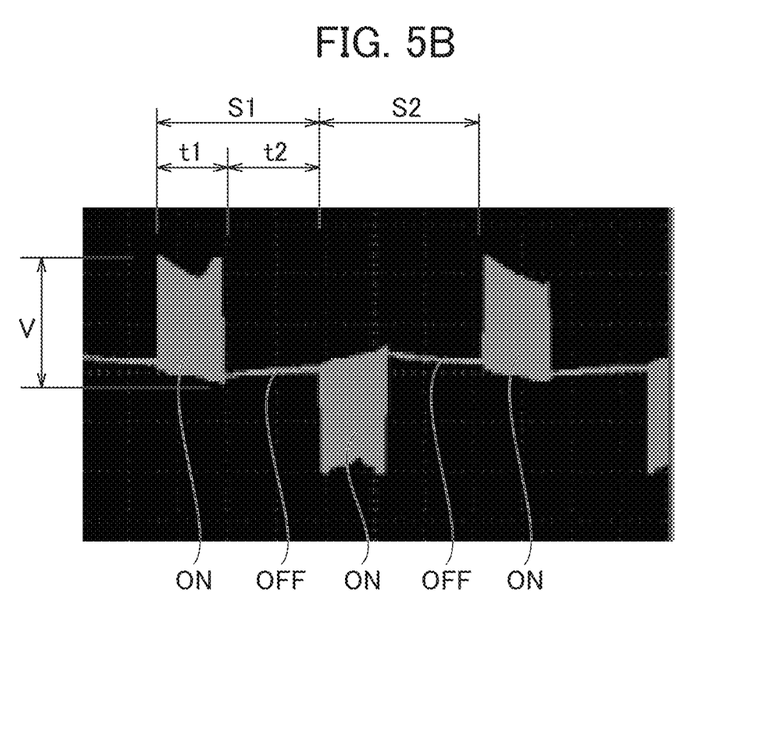
FIG. 5B is a diagram illustrating a synthesized waveform on an output side of an output transformer when a pad is actually applied to a living body.

FIG. 5A illustrates an example of an output signal of the high-frequency signal generator 5, and illustrates a high-frequency signal of 2 μsec and 500 kHz. FIG. 5B illustrates a synthesized waveform on the output side of the output transformer 8 when the pads 9 are actually applied to the living body 10. The output side of the output transformer 8 is isolated from the synthesizer 7 on the primary side (the input side), and charging/discharging characteristics of the applied voltage change depending on changes in the reactance characteristics of the output transformer 8 and the capacitance characteristics of the living body 10. Therefore, the actual waveform characteristics are different from that in the theoretical synthesized waveform diagram illustrated in FIG. 2B, and have a shape close to the waveform illustrated in FIG. 6.

Figure 2C:
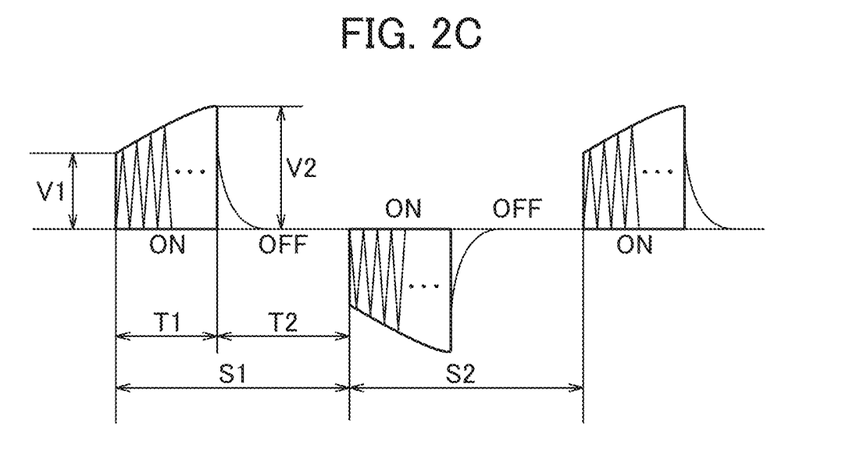
FIG. 2C is a diagram illustrating a synthesized waveform in which a level of the high-frequency signal superimposed on the low-frequency pulse signal wave gradually increases or decreases during an ON period.

When the pads 9 connected to the secondary coil Lo of the output transformer 8 are attached to the living body, the signal waveform on the output side during the ON period of the synthesized waveform is charged and discharged according to the time constants of the capacitive reactance (capacitor) components Co and C (including a reactance between the pads 9 and the living body) of the living body and the resistance components ro, r, and R. If the time constant on the output side of the output transformer 8 is set to have a value that the high-frequency signal of 500 kHz is not discharged immediately by the capacitive reactance component, the synthesized waveform signal keeps rising during the ON period. Therefore, in the synthesized waveform on the output side of the output transformer 8, as illustrated in the synthesized waveform (secondary side) of FIG. 2C, the voltage level of the superimposed high frequency gradually rises during the ON period of the primary cycle S1, and as illustrated in the t1 period, when the voltage level rises from the V1 level as initial rise to reach the V2 level, the level stops rising, and the superimposed high frequency is not observed. That is, the waveform of the synthesized waveforms forms a sword-shape by gradually increasing, instead of forming a rectangular shape. In the next cycle S2, the vertical direction is reversed, and thus, it is shaped such that the vertical direction of S1 is reversed.

In addition, in the time constant setting on the secondary side of the output transformer, the line resistance R is adjusted to avoid an overshoot or an undershoot that may be caused by rising or falling during the ON period respectively. That is, on the output side of the output transformer 8, an integrating circuit is set to be formed for the synthesized waveform instead of a differentiating circuit in a state where the pads 9 are attached to the living body. That is, when one or more pairs of pads 9 connected to the output side of the output transformer 8 are attached to the living body 10, an impedance on the output side of the output transformer 8 is set such that the voltage of the synthesized waveform gradually increases and decreases during the ON period of the synthesized waveform on the output side of the output transformer 8. In order to perform these settings easily, the line resistance R may be a semi-fixed resistance or a variable resistance. This can eliminate the occurrence of the overshoot or the undershoot, and thus, the pain or a sense of discomfort caused by noise can be eliminated. Further, it is not necessary to provide a complicated circuit as disclosed in Patent Document 5.

Figure 3:
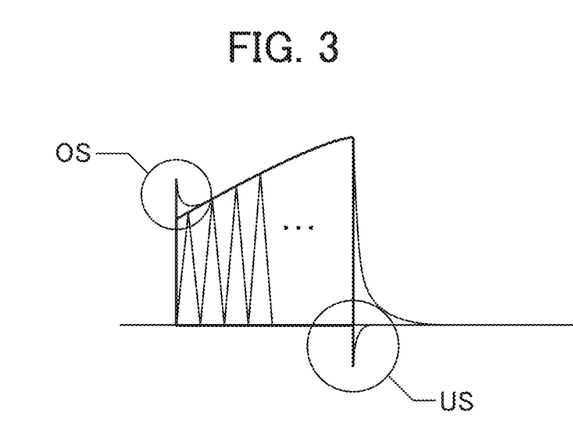
FIG. 3 is a diagram illustrating an overshoot and an undershoot of the synthesized waveform.

By configuration as above, time constants by a reactance component of the living body and the resistance components on the secondary side of the output transformer 8 are adjusted without forming the synthesized waveform in which a rectangular wave and a triangular wave are synthesized with the low-frequency pulse on the primary side of the output transformer 8. Accordingly, it is possible to form a waveform in which a level gradually increases or decreases instead of forming the rectangular waveform and such waveform can be applied to the living body 10. Therefore, since it is not necessary to deform the synthesized waveform on the primary side of the output transformer 8, a circuit for generating the triangular wave to be superimposed on the low-frequency rectangular wave pulse as illustrated in the conventional technique (Patent Document 5) is not required, and it is possible to configure with a simple circuit. Further, as illustrated in FIG. 3, the noise, overshoot OS, and undershoot US caused when synthesizing the rectangular wave pulse and the triangular wave are reduced, and a waveform providing a soft touch can be formed.

Figure 6:
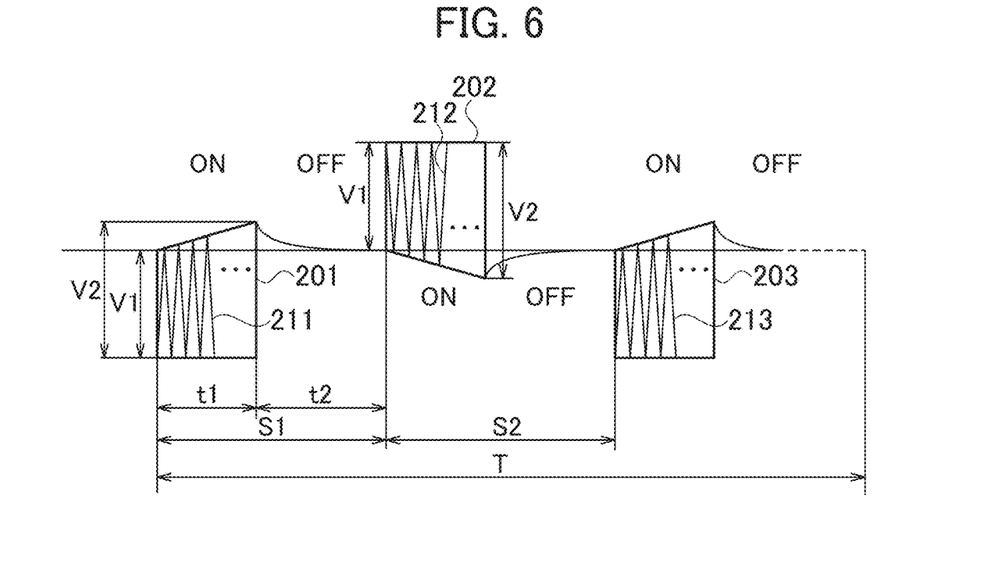
FIG. 6 is an explanatory diagram illustrating a variable synthesized waveform generated by the living body stimulator according to the embodiment.

The synthesized waveform illustrated in FIG. 6 is a waveform that is actually applied to the living body, and the level of the superimposed high-frequency signal wave 211 gradually rises during the ON period t1 of the primary cycle S1, the level rises from the V1 level as initial rise as illustrated in the t1 period and after the level reaching the V2 level, the level stops rising and the superimposed high-frequency signal wave 211 is not observed. That is, the synthesized waveform has a shape of gradually increasing instead of having a rectangular wave shape. After an elapse of an end of the ON period t1, the superimposed high-frequency signal wave 211 is not observed, and a period is shifted to a rest period of the OFF period (t2). In a next cycle S2, a vertical direction of the cycle S1 is reversed.

A synthesized waveform obtained by synthesizing the high-frequency signal waves 211, 212, 213, . . . and the low-frequency pulse signal waves 201, 202, 203, . . . illustrated in FIG. 6 is used as a basic waveform. As described above, the formed basic waveform is used as a continuous wave of only on the upper side (in the positive direction) or only on the lower side (in the negative direction) of the synthesized waveform signal, and waveforms of various modes depending on the use purpose are formed by switching the upper side (the positive direction) and the lower side (the negative direction) of the synthesized waveform signal for each cycle or at every several cycles, or by providing a rest period in the middle. By repeating the application of the basic waveform of synthesized waveform of FIG. 6 to the living body continuously for a predetermined period of time (T period), and again, the application of the basic waveform of synthesized waveform with a rest period being interposed between the applications, stimulation effects on the inner muscle by the high-frequency component and stimulation effects on the outer muscle by the low frequency component can be expected.

However, while the synthesized waveform is effective mainly for applying the living body stimulation to the inner muscle, the stimulation effect of the synthesized waveform on the outer muscle may not be expected that much. If the use purpose of the device is the trunk strengthening and muscle tightening, it is necessary to stimulate more strongly not only the inner muscle but also the outer muscle at the same time. Therefore, in the embodiment, the cyclic change by a low-frequency cycle is applied to the above described basic waveform of the synthesized waveform.

Figure 7:
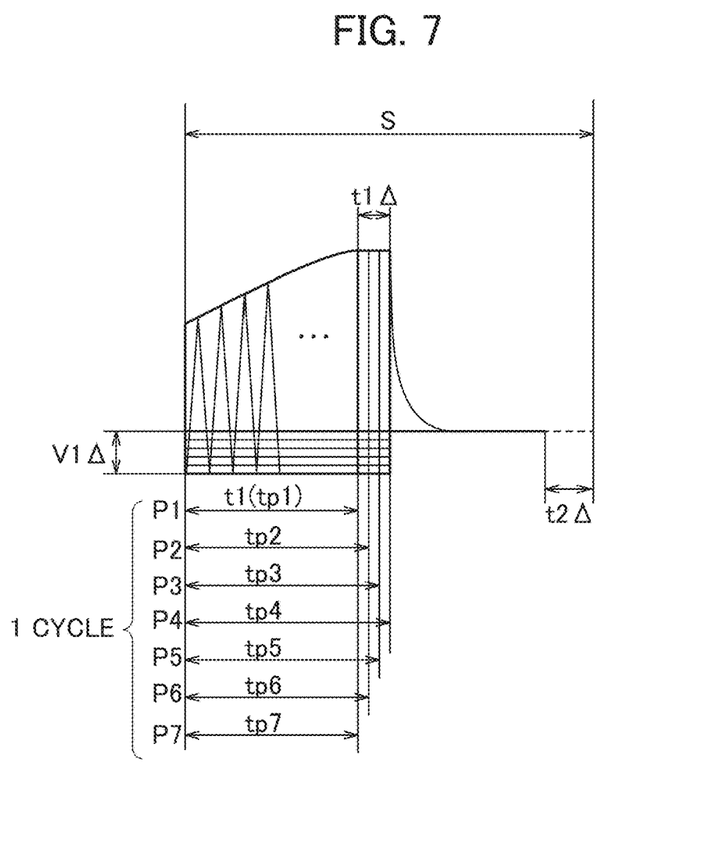
FIG. 7 is a waveform explanatory diagram of a variable synthesized waveform in which a synthesized waveform obtained by synthesizing a high-frequency signal wave with a low-frequency pulse signal wave is varied at a low-frequency cycle temporarily (cyclically) in terms of level.

FIG. 7 is a waveform explanatory diagram of a variable synthesized waveform obtained by varying a synthesized waveform in which a high-frequency signal wave and a low-frequency pulse signal wave are synthesized temporarily (cyclically) in terms of level at a low-frequency cycle. If the synthesized waveform is to be temporarily varied in FIG. 7, the waveform control signal circuit 6 temporarily varies the ON period (a period in which the high-frequency signal and the low-frequency pulse signal are synthesized) of the synthesized waveform by the period t1Δ at a low-frequency cycle. As illustrated in FIG. 7, the waveform control signal circuit 6 sets the ON periods tp1, tp2, tp3, tp4, tp5, tp6, and tp7 as one cycle length, and temporarily varies the ON period at a low-frequency cycle to form a variable synthesized waveform. Further, even if a period is an OFF period (a period in which the high-frequency signal wave is not synthesized with the low-frequency pulse signal wave), the waveform control signal circuit 6 generates a variable synthesized waveform by temporarily varying the OFF period by a period t2Δ at a low-frequency cycle. With respect to the temporal variation at the low-frequency cycle, the ON period t1 may be randomly varied by the period t1Δ and the OFF period t2 may be randomly varied by the period t2Δ, or the entire continuous predetermined period (T period) of the synthesized waveform may be varied at the low-frequency cycle, so that the individual cycle periods of the synthesized waveform (S1, S2, S3, . . . ) are simultaneously varied at the same cycle period.

No problem is caused if a cycle of a temporal variation is the low-frequency cycle and is in a range of generating the stimulation effect on the outer muscle, and the cycle is not particularly specified to the low-frequency cycle. In the embodiment, the output time of the ON period is randomly changed in a range from 100 μsec to 500 μsec, and the repetition width (S period) is randomly changed in a range from 100 μsec to 500 μsec. That is, the entire continuous predetermined period (T period) of the varying synthesized waveform is randomly varied at the low-frequency cycle. By the synthesized waveform being varied at the low-frequency cycle, the synthesized waveform forms a waveform similar to a state in which a pulse width modulation is given, and the synthesized waveform causes the variation (or waviness) of the low-frequency cycle to be generated. The variation of the low-frequency cycle further enhances the stimulation effect on the outer muscle.

In this way, the variable synthesized waveform group is configured in which the ON period t1, the OFF period t2, or the repetition cycle length S is varied at the low-frequency cycle, and the continuous predetermined period T of the synthesized waveform is variable. In this case, the waveform control signal circuit 6 makes a control so that at least a part of the synthesized waveform is formed of the variable synthesized waveform group which forms a state in which at least one of the ON period and the OFF period is varied at the low-frequency cycle. This enables the continuous obtaining of effects of stimulating both the outer muscle by the variation at the low-frequency cycle and the inner muscle by the high-frequency signal wave.

In a case of a fixed synthesized waveform group in which the temporal variation at the low-frequency cycle is not performed and the repetition cycle length S and the predetermined period T of the synthesized waveform are fixed, although the living body stimulation on the inner muscle is strengthened, the stimulation effect on the outer muscle is slight. To obtain effects of the muscle training and muscle tightening, by using the variable synthesized waveform group and the fixed synthesized waveform group in combination, effective living body stimulation can be provided to the inner muscle and the outer muscle used during the trunk training such as an abdominal muscle exercise and a weight load exercise and a muscle tightening exercise.

When a level (amplitude) variation is applied, as illustrated in FIG. 7, the waveform control signal circuit 6 controls the synthesizer 7 so as to configure the variable synthesized waveform group in which the output level of the ON period (a period in which the high-frequency signal and the low-frequency pulse signal are synthesized) of the synthesized waveform is increased/decreased by V1Δ at the low-frequency cycle and is varied. In the level variation, each ON period forming the synthesized waveform may be randomly increased or decreased, or the continuous cycle length S and the ON periods of the entire predetermined period T of the synthesized waveform may be varied in terms of level at the low-frequency cycle. The level to be varied depends on the application level intensity of the synthesized signal, but the effect is obtained with about 5% to 40% of the total. By randomly changing the amount of change, fixing the amount, or adjusting the amount of change manually so as to set the amount to the amount of change that the user feels comfortable depending on the use purpose or the physical sensation, the same effect as the temporal variation described above can be obtained.

In the embodiment, the output level during the ON period is increased and decreased 5 times per second by about 20% of the total amplitude to promote the muscle contraction of 5 times per second. This generates a waveform equivalent to the synthesized waveform applied with the amplitude modulation by the low frequency, and the stimulation effect on the outer muscle can be increased. Both the level variation and the above described temporal variation may be used, or either one of them may be used.

In this manner, by configuring the variable synthesized waveform group that forms a state in which, among the continuous predetermined period (T period) of the synthesized waveform, at least one of the ON period and the OFF period is varied at the low-frequency cycle, it is possible to obtain an effect of stimulating both the outer muscle by the low-frequency cycle variation and the inner muscle by the high-frequency signal wave. Further, in the case of the fixed synthesized waveform group in which the temporal variation and the level variation are not performed at the low-frequency cycle and the period and the level are fixed, while the living body stimulation on the inner muscle is strengthened, the stimulation effect on the outer muscle is slight. To obtain effects of the muscle training and muscle tightening, by using the variable synthesized waveform group and the fixed synthesized waveform group in combination, effective living body stimulation on the inner muscle and the outer muscle used for the trunk training such as the abdominal muscle exercise and weight load exercise and the muscle tightening exercise can be obtained.

Figure 8A:
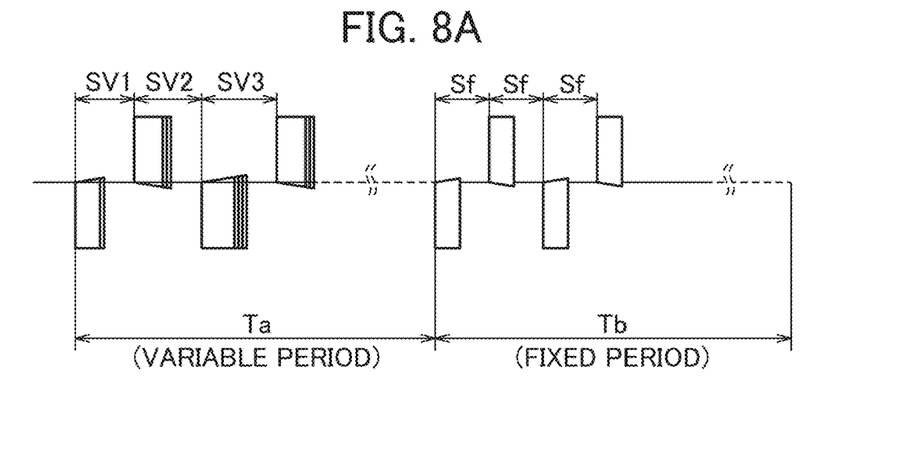
FIG. 8A is a diagram illustrating a living body stimulation waveform in which a variable period Ta of a variable synthesized waveform group and a fixed period Tb of a fixed synthesized waveform group are combined.
Figure 8B:
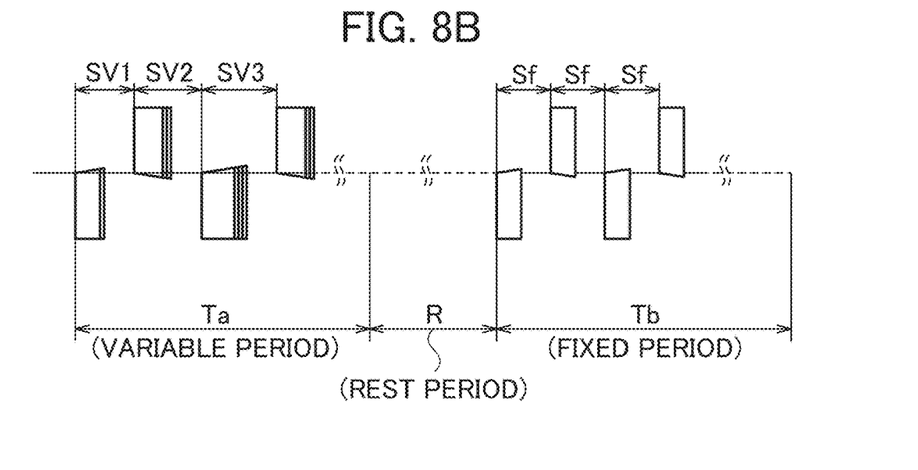
FIG. 8B is a diagram illustrating a living body stimulation waveform in which a slight rest period R is provided between the variable period Ta of the variable synthesized waveform group and the fixed period Tb of the fixed synthesized waveform group.
Figure 8C:
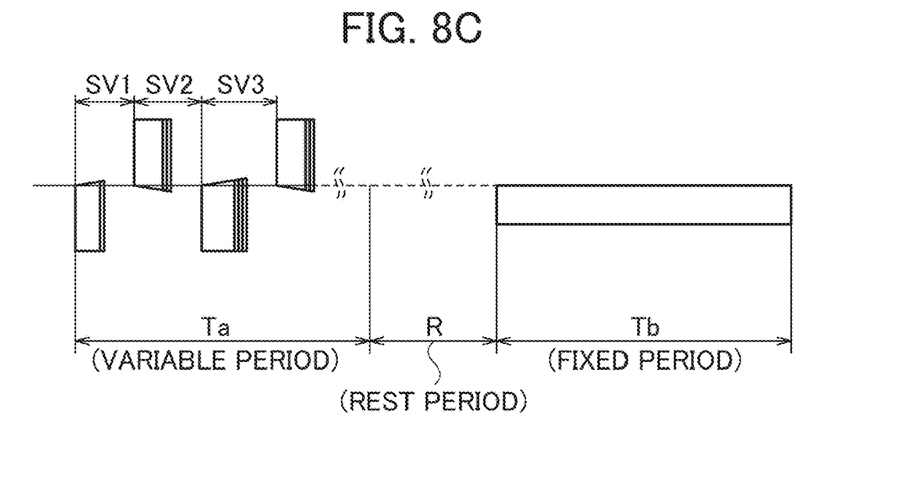
FIG. 8C is a diagram illustrating a living body stimulation waveform formed by replacing the fixed synthesized waveform group in FIG. 8B with continuous high-frequency signal components.

Each of FIGS. 8A to 8C is an explanatory diagram illustrating a combination example of the waveform of the fixed synthesized waveform group illustrated in FIG. 6 and the variable synthesized waveform illustrated in FIG. 7. A living body stimulation waveform illustrated in FIG. 8A is a combination of a variable period Ta of the variable synthesized waveform group and a fixed period Tb of the fixed synthesized waveform group, and the variable period Ta and the fixed period Tb are repeated several times without providing a rest period between the variable period Ta and the fixed period Tb. The variable period Ta consists of a plurality of variable synthesized waveforms having different cycle lengths Sv1, Sv2, and Sv3. The fixed period Tb consists of a plurality of variable synthesized waveforms having fixed cycle lengths Sf. A living body stimulation waveform illustrated in FIG. 8B is configured by providing a slight rest period R (every few seconds) between the variable period Ta of the variable synthesized waveform group and the fixed period Tb of the fixed synthesized waveform group. Further, as another combination, a living body stimulation waveform illustrated in FIG. 8C can be formed by replacing the fixed synthesized waveform group illustrated in FIG. 8B with the continuous high-frequency signal components. In either case, the variable period of the variable synthesized waveform group, the fixed period of the fixed synthesized waveform group, the rest period, and the low-frequency variable cycle are used in combination so as to be most effective depending on the use purpose.

Next, a description will be given for the setting and effects of modes of the muscle training/muscle tightening using the living body stimulator according to the embodiment. FIG. 5B illustrates a secondary output waveform of the output transformer 8 in examples of the modes of the muscle training/muscle tightening, and is a synthesized waveform (a basic waveform) of the high-frequency signal waveform and the low-frequency pulse signal. The measurement is made by simulating the output waveform with a dummy resistances of 500Ω (R1, R2). As a variable synthesized waveform for this basic waveform (fixed synthesized waveform), a high-frequency signal wave of 500 kHz and a rectangular wave pulse as a low-frequency pulse signal wave are used, an ON period t1 is varied randomly from a few seconds to 10 seconds at a low-frequency cycle, an OFF period t2 is varied from 2 seconds to 5 seconds, and an output level V1 is set to be adjustable with several mV.

Figure 9:
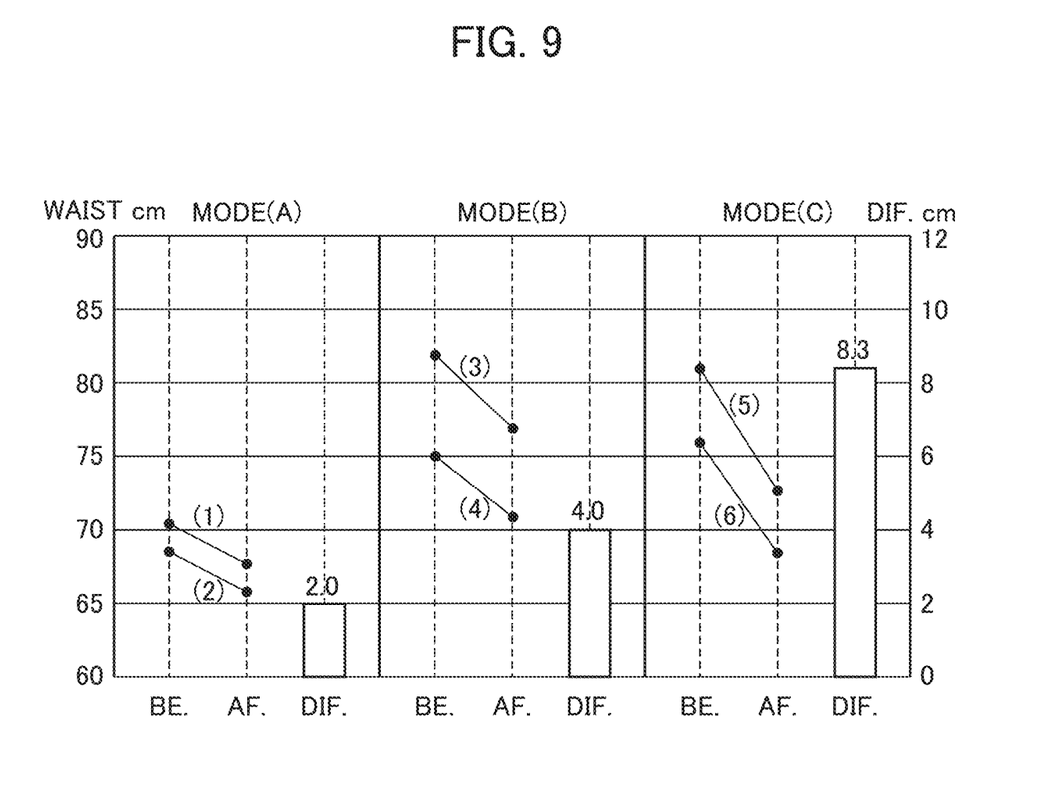
FIG. 9 is data illustrating an example of an effect of a muscle training using the living body stimulator according to the embodiment.

FIG. 9 illustrates the measurement results of effects of the muscle strengthening and muscle tightening by using the living body stimulator according to the embodiment based on the above setting. In FIG. 9, the living body stimulator is applied to the iliopsoas muscle stimulation around the waist. The iliopsoas muscle is a group of deep abdominal muscles in the deep trunk composed of the psoas major and iliac muscles, and has the functions of the hip joint as an inner muscle. Therefore, the iliopsoas muscle is a muscle necessary for walking, various kinds of exercise, and posture maintenance, and if the iliopsoas muscle is weakened or damaged due to injury or aging, such weakening and damage will lead to gait disorder and reduction in the exercise performance. In the measurement of FIG. 9, a conventional synthesized waveform not applied with a variation at the low-frequency cycle and a waveform composed of the variable period Ta and the fixed period Tb as illustrated in FIG. 8A, which is applied with a variation at the low-frequency cycle are used. With respect to the waveform parameters of the variable period, the high-frequency signal fh is 500 kHz, the ON period t1 of the low-frequency pulse is randomly varied from 150 to 400 μsec, and the repetitive cycle S is temporally varied from 160 to 550 μsec. No level variation is applied to the ON period.

FIG. 9 is a comparative view in which the muscle training and the shape-up (muscle tightening) are set, three modes are set by combining the variable synthesized waveform group and the fixed synthesized waveform group and changing the application time of the waveforms, and the change in the waist circumference relative to each parameter change is measured before and after the application of the living body stimulator according to the embodiment. The waist circumference is a part at which effects of shape-up are most remarkable observed during a short period of time. Therefore, the change tendency of the living body stimulator according to the embodiment can be easily measured. The high-frequency signal wave applied to all cases is the high-frequency signal wave of 500 kHz, and the low-frequency pulse signal wave of 5 to 40 Hz is applied for 20 minutes continuously to obtain data on the waist circumference before and after the application.

In a mode A, as illustrated in FIG. 6, a conventionally used basic synthesized waveform group in which the high-frequency signal is merely superimposed on the low-frequency pulse is used, and only the fixed synthesized waveform group not applied with the variation at the low-frequency cycles is applied to two test subjects (1) and (2) continuously for 20 minutes, and the change in the waist circumferences before and after the application is illustrated. According to this measurement, the waist circumferences of both test subjects (1) and (2) are reduced, and the effect of this mode A was that the difference (right scale) of the waist circumferences between before and after the application was 2 cm reduced in average.

A mode B uses the waveform configuration illustrated in FIG. 8A, the application time of the variable synthesized waveform group is set to be (Ta=4 seconds), and the application time of the fixed synthesized waveform group is set to be (Tb=4 seconds), the waveform groups are applied to two test subjects ((3) and (4)) consecutively for 20 minutes, and the changes in waist circumference before and after the application are illustrated. According to this measurement, the waist circumferences of both test subjects (3) and (4) are reduced, and the effect of the mode B is that the difference in the waist circumferences between before and after the application (right scale) is 4 cm reduced in average.

A mode C uses the waveform configuration illustrated in FIG. 8B, the application time of the variable synthesized waveform group is set to be (Ta=4 seconds), the application time of the fixed synthesized waveform group is set to be (Tb=2 seconds), and the waveform groups are applied to two test subjects ((5) and (6)) continuously for 20 minutes to obtain the changes in the waist circumference before and after the application. According to this measurement, the waist circumferences of both test subjects (5) and (6) are significantly reduced, and the effect of the mode C is that the difference in the waist circumferences between before and after the application (right scale) is 8.3 cm reduced in average.

In the comparison of these 3 modes, the application of the combination of the variable synthesized waveform group and the fixed synthesized waveform (modes B and C) is more effective in increasing the muscle strength or in the shape-up (the muscle tightening) than the application of only the fixed synthesized waveform group (mode A). In the combination of the variable synthesized waveform group and the fixed synthesized waveform group, the waist circumference shortening effect was more observed in the mode C in which the application time of the variable synthesized waveform group is set to be 4 seconds and the application time of the fixed synthesized waveform group to set to be 2 seconds, than in the mode B in which the application times of both of the variable synthesized waveform group and the fixed synthesized waveform are the same and are set to be 4 seconds.

The shortening of the waist circumference is used as an index of the trunk strengthening measurement because effects of the shortening of the waist circumference are observed during a comparatively short time in the muscle training, and the shortening of the waist circumference is regarded as expressing the strengthening of the inner muscle and the outer muscle. By applying, to the living body, the synthesized waveform group in which the high-frequency signal wave and the low-frequency pulse are superimposed, the living body stimulation reaching the inner muscle can be obtained, and by configuring the variable synthesized waveform group in which the synthesized waveform is varied at the low-frequency cycle and combining the variable synthesized waveform group with the fixed synthesized waveform group, it is observed that a stimulation effect can be obtained not only on the inner muscle but also on the outer muscle. That is, for the muscle training and the muscle tightening, not only the inner muscle but also the outer muscle is stimulated, so that an effective effect can be obtained by strengthening the trunk and by the shape-up.

According to the embodiment, in a state where the variable synthesized waveform group is applied, the outer muscle and the inner muscle are stimulated, and thus, it is assumed that a signal corresponding to a nerve impulse is applied basically to almost all muscle fibers by an exercise load, and the exercise intensity becomes at least 50% RM or above of the maximum muscle force. Further, in a state where the fixed synthesized waveform group is applied, while the stimulation effect on the outer muscle is small, only the stimulation effect on the inner muscle continues to be remarkable. Further, the stimulation on the inner muscle by the high-frequency signal component becomes weaker than the stimulation effect on the outer muscle by the low-frequency signal component, and thus, it is desirable to continue the stimulation on the inner muscle as long as possible.

Accordingly, for the living body stimulation waveform, if the variable synthesized waveform group and the fixed synthesized waveform group are combined, by taking an assumption of Hettinger theory into consideration, it is effective to set the application times of the variable synthesized waveform group and the fixed synthesized waveform group to be about 2 to 15 seconds in total, and to repeat the application, and it is assumed that more effective results can be obtained by setting the application time of the variable synthesized waveform group to be longer than the application time of the fixed synthesized waveform group. As the effects of the demonstration experiment that take these assumptions into consideration, it is observed that the maximum effect is obtained if especially the application time of the variable synthesized waveform group is set to be in a range from 2 to 10 seconds, and the application time of the fixed synthesized waveform group is set to be in a rage from 1 to 4 seconds. From the above, it is found that the stimulation of the synthesized waveform in the living body stimulator requires a slight rise of about 1 to 2 seconds to start the muscle contraction, and with respect to the application time, as similar to the exercise load in the Hettinger theory, the muscle becomes accustomed and gradually becomes stiffened if the muscle continues to contract, so the effect may be obtained by applying a change in a range from about 10 to 15 seconds.

The living body stimulator according to the embodiment can be applied to the above described modes and the like of the muscle training and the muscle tightening (the shape-up), so as to enable the muscle stimulation reaching the inner muscle by a synthesized waveform in which the high-frequency signal wave and the low frequency are synthesized with a simpler configuration. The application of the variable synthesized waveform group configured by applying the variation at the low-frequency cycle to the synthesized waveform is more effective for strengthening the trunk muscle, and the optimum combination time of the variable synthesized waveform group and the fixed synthesized waveform group is applied. As a result, very high effects on the muscle training and the muscle tightening can be efficiently obtained, and the industrial applicability is high.

What is claimed is:

1. A living body stimulator, comprising:
a low-frequency pulse generator configured to generate a low-frequency pulse signal wave;
a high-frequency signal generator configured to generate a high-frequency signal wave;
a synthesizer configured to form a synthesized waveform in which the high-frequency signal wave generated by the high-frequency signal generator is superimposed on the low-frequency pulse signal wave generated by the low-frequency pulse generator, and apply an electrical stimulation by the synthesized waveform to a living body;
a controller configured to control the synthesizer so that one cycle is configured from an ON period of the synthesized waveform in which the high-frequency signal wave is superimposed on the low-frequency pulse signal wave and an OFF period in which the high-frequency signal wave is not superimposed on the low-frequency pulse signal wave; and
an output transformer configured to receive the synthesized waveform, wherein
an impedance on an output side of the output transformer is set such that a voltage of the synthesized waveform gradually increases and decreases during the ON period of the synthesized waveform on the output side of the output transformer when one or more pairs of pads connected to the output side of the output transformer are attached to the living body, and an integrating circuit is formed for the synthesized waveform on the output side of the output transformer in a state where the pads are attached to the living body,
the controller is configured to control the synthesizer such that at least a part of the synthesized waveform is configured from a variable synthesized waveform group in which at least one of the ON period and the OFF period has been varied at a low-frequency cycle or in which an amplitude level of the high-frequency signal wave of the ON period has been varied at the low-frequency cycle,
a living body stimulation waveform for applying the synthesized waveform to the living body is a repetitive waveform formed from a combination of the variable synthesized waveform group and a fixed synthesized waveform group in which the ON period and the OFF period are fixed,
the living body stimulation waveform is formed from a combination of the variable synthesized waveform group with an application time of 2 to 10 seconds and the fixed synthesized waveform group with an application time of 1 to 4 seconds, and
a rest period is provided between a period of the variable synthesized waveform group and a period of the fixed synthesized waveform group.

2. The living body stimulator of claim 1, wherein a period of the fixed synthesized waveform group is set to be in a range from 40% to 100% of a period of the variable synthesized waveform group.

* * * * *